United States Patent
Ali et al.

(10) Patent No.: US 9,771,657 B2
(45) Date of Patent: *Sep. 26, 2017

(54) COMPOSITIONS FOR CORROSION INHIBITION

(71) Applicant: KING FAHD UNIVERSITY OF PETROLEUM AND MINERALS, Dhahran (SA)

(72) Inventors: Shaikh Asrof Ali, West Midnapore (IN); Mohammad Abu Jafar Mazumder, Hamilton (CA); Hasan Ali Al-Muallem, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 0 days.

This patent is subject to a terminal disclaimer.

(21) Appl. No.: 15/488,091

(22) Filed: Apr. 14, 2017

(65) Prior Publication Data
US 2017/0218523 A1    Aug. 3, 2017

Related U.S. Application Data

(63) Continuation of application No. 14/525,513, filed on Oct. 28, 2014.

(51) Int. Cl.
*C23F 11/04* (2006.01)
*C07D 261/02* (2006.01)

(52) U.S. Cl.
CPC ............ *C23F 11/04* (2013.01); *C07D 261/02* (2013.01)

(58) Field of Classification Search
CPC .............................. C23F 11/149; C23F 11/04
See application file for complete search history.

(56) References Cited

U.S. PATENT DOCUMENTS

| 4,762,627 A | 8/1988 | Martinez et al. |
| 5,120,471 A | 6/1992 | Jasinski et al. |
| 2006/0247135 A1 | 11/2006 | Welton et al. |
| 2007/0071887 A1 | 3/2007 | Cassidy et al. |

FOREIGN PATENT DOCUMENTS

CN    103289663 A    9/2013

OTHER PUBLICATIONS

Mazumder et al. Design and synthesis of a novel class of inhibitors for mild steel corrosion in acidic and carbon dioxide-saturated saline media. Corrosion Science 87 187-198. Jun. 18, 2014.*
Mazumder, et al., Design and synthesis of a novel class of inhibitors for mild steel corrosion in acidic and carbon dioxide-saturated saline media. Corrosion Science 87 187-198. Jun. 18, 2014

* cited by examiner

*Primary Examiner* — Sean E Conley
*Assistant Examiner* — Donald Spamer
(74) *Attorney, Agent, or Firm* — Oblon, McClelland, Maier & Neustadt, L.L.P.

(57) ABSTRACT

Compounds and methods of inhibiting corrosion of mild steel. Compounds disclosed herein are cationic and contain multiple functional motifs such as propargyl, cinnamaldehyde, isoxazolidine and hydrophobe. These compounds are found to be effective in inhibiting mild steel corrosion in HCl, $H_2SO_4$, NaCl and $CO_2$-saturated environments.

8 Claims, 6 Drawing Sheets

COMPOSITIONS FOR CORROSION INHIBITION

The present application is a continuation application of Ser. No. 14/525,513, now allowed, having a filing date of Oct. 28, 2014.

BACKGROUND OF THE INVENTION

Technical Field

The present invention relates to compounds that inhibit corrosion of mild steel and methods thereof. More specifically, the present invention relates to compounds containing multiple functional motifs for arresting mild steel corrosion, methods of synthesizing the compounds and methods of preventing corrosion of mild steel with the compounds.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Mild steel is the least expensive and most commonly used among all steel alloys. Mild steel is weldable, very hard and durable, despite the fact that it rusts easily. Containing a maximum of 0.29% carbon, mild steel is able to be magnetized and is used in almost any project that requires a vast amount of metal.

Many of the everyday objects that are created from steel are made using mild steel, including automobile chassis, motorcycle frames and most cookware. Due to its poor corrosion resistance, mild steel must be painted or otherwise protected and sealed in order to prevent rust from damaging it. A light coat of oil or grease is able to seal this steel and aid in rust control.

Most of the pipelines in the world are made of mild steel which not only allows the pipe to be easily welded into place, but also lets the pipeline flex to avoid cracking and breaking under pressure.

The corrosion of mild steel pipelines constitutes a significant portion (~30%) of the economic losses in the oil and gas industry (W. Durnie, B. Kinsella, R. De Marco, A. Jefferson, Structure activity of oil field corrosion inhibitors, J. Electrochem. Soc. 146 (1999) 1751-1756; F. Bentiss, M. Lagrenee, M. Traisnel, 2, 5-bis(n-pyridyl)-1 3,4-oxadiazoles as corrosion inhibitors for mild steel in acidic media, Corrosion 56 (2000) 733-742; V. S. Sastri, Corrosion Inhibitors, Principles and Application, John Wiley and Sons, Chichester, UK, 1998—each incorporated herein by reference in its entirety). Crude oil itself is corrosive; carbon dioxide, present in gas or injected into oil wells to increase its production, is also corrosive (X. Jiang, Y. G. Zheng, D. R. Qu, W. Ke, Effect of calcium ions on pitting corrosion and inhibition performance in $CO_2$ corrosion of N80 steel, Corros. Sci. 48 (2006) 3091-3108—incorporated herein by reference in its entirety). Mild steel also undergoes severe corrosive attack during industrial acid cleaning.

The corrosive attack in the HCl medium is explained using the following Reactions 1-5 occurring at anode and Reactions 6-9 occurring at cathode (M. Morad, J. Morvan, J. Pagetti, 'Proceedings of the 8th European Symposium on Corrosion Inhibitors (8 SEIC)', Ann. Univ. Ferrara, N. S., Sez V, Suppl: N. 10:159, 1995; K. Aramaki, N. Hagiwara, H. Nishihara, The synergistic effect of anions and the ammonium cation on the inhibition of iron corrosion in acid solution, Corros. Sci. 27 (1987) 487-497—each incorporated herein by reference in its entirety):

Anodic Dissolution of Fe:

$$Fe + Cl^- \rightleftharpoons (FeCl^-)_{ads} \quad \text{(Reaction 1)}$$

$$(FeCl^-)_{ads} \rightleftharpoons (FeCl)_{ads} + e^- \quad \text{(Reaction 2)}$$

$$(FeCl)_{ads} \rightarrow FeCl^+ + e^- \quad \text{(Reaction 3)}$$

$$FeCl^+ \rightleftharpoons Fe^{2+} + Cl^- \quad \text{(Reaction 4)}$$

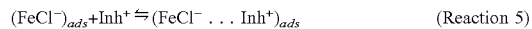

$$(FeCl^-)_{ads} + Inh^+ \rightleftharpoons (FeCl^- \ldots Inh^+)_{ads} \quad \text{(Reaction 5)}$$

Cathodic Evolution of $H_2$:

$$Fe + H^+ \rightleftharpoons (FeH^+)_{ads} \quad \text{(Reaction 6)}$$

$$(FeH^+)_{ads} + e^- \rightarrow (FeH)_{ads} \quad \text{(Reaction 7)}$$

$$(FeH)_{ads} + H^+ + e^- \rightarrow Fe + H_2 \quad \text{(Reaction 8)}$$

$$Fe + Inh^+ \rightleftharpoons (FeInh^+)_{ads} \quad \text{(Reaction 9)}$$

The detrimental reactions are retarded by consecutive adsorption of a chloride ion and a cationic inhibitor ($Inh^+$) as described in Reaction 5 which restricts Reactions 2-4. The corrosion by cathodic evolution of hydrogen, on the other hand, can be minimized by effective competition of the $Inh^+$ with $H^+$ (Reaction 6 vs. Reaction 9).

The nature of anions is known to influence the efficiency of corrosion inhibition by ammonium salts (F. Bentiss, M. Lagrenee, M. Traisnel, J. C. Hornez, The corrosion inhibition of mild steel in acidic media by a new triazole derivative, Corros. Sci. 41 (1999) 789-803—incorporated herein by reference in its entirety). While anions are excellent inhibitors in HCl, they are, however, poor inhibitors in $H_2SO_4$ (T. Murakawa, N. Hackerman, The double layer capacity at the interface between iron and acid solutions with and without organic materials, Corros. Sci. 4 (1964) 387-397—incorporated herein by reference in its entirety). The positive surface charge of iron in both acidic media, because of the corrosion potential $E_{corr}$ being more positive than the potential for zero charge (PZC) $E_{q=0}$, discourages the adsorption of organic cations (L. I. Antropov, Zhurnal Fizicheskoi Khimii, The application of the potential scale to the problem of the corrosion and protection of metals, 37 (1963) 965-978—incorporated herein by reference in its entirety). However, the stronger adsorbability of the $Cl^-$ in compare to $SO_4^{2-}$ (S. Rengamani, S. Muralidharan, M. A. Kulandainathan, S. V. Iyer, Inhibiting and accelerating effects of amino phenols on the corrosion and permeation of hydrogen through mild-steel in acidic solutions, J. Appl. Electrochem. 24 (1994) 355-360; J. O'M. Bockris, B. Yang, The mechanism of corrosion inhibition of iron in acid solution by acetylenic alcohols, J. Elctrochem. Soc. 138 (1991) 2237-2252; W. J. Lorenz, Zeitschrift fuer Physikalische Chemie (Leipzig), Theory of partial charge transfer reactions 244 (1970) 65-84—each incorporated herein by reference in its entirety), shifts the PZC ($E_{q=0}$) to more positive values than the $E_{corr}$ thereby allowing the electrostatic adsorption of inhibitor ions $Inh^+$. The film of $(FeCl^- \ldots Inh^+)_{ads}$ imparts protection against corrosive HCl media. The inhibitive efficiencies of organic cationic inhibitors in $H_2SO_4$ media increases significantly in the presence of halide ions (A. Popova, E. Sokolova, S. Raicheva, M. Chirstov, AC and DC study of temperature effect on mild steel corrosion in acid media in presence of benzimidazole derivatives, Corros. Sci. 45 (2003) 33-58—incorporated herein by reference in its entirety). Since the first introduction of isoxazolidines to the corrosion literature (S. A. Ali, M. T. Saeed, S. U. Rahman, The isoxazolidines: a new class of corrosion inhibitors of mild steel in acidic medium, Corros. Sci. 45 (2003) 253-266—incorporated herein by reference in its entirety), continued efforts have established that these compounds bearing long chain hydrophobic substituents are effective inhibitors both in $H_2SO_4$ and HCl media (S. A. Ali, A. M. El-Shareef, R. F. Al-Ghamdi, M. T. Saeed, The isoxazolidines: the effects of steric factor and hydrophobic chain length on the corrosion inhibition of mild steel in acidic medium, Corros. Sci. 47 (2005) 2659-2678; S. A. Ali, H. A. Al-Muallem, M. T. Saeed, S. U. Rahman, Hydrophobic-tailed bicycloisoxazolidines: A comparative study of the newly synthesized compounds on the inhibition of mild steel corrosion in hydrochloric and sulfuric acid media', Corros. Sci. 50 (2008) 664-675; S. A. Ali, H. A. Al-Muallem, S. U. Rahman, M. T. Saeed, Bis-Isoxazolidines: a new class of corrosion inhibitors of mild steel in acidic media, Corros. Sci. 50 (2008) 3070-3078—each incorporated herein by reference in its entirety). Diallylamines bearing long chain hydrophobe and alkyne substituents also imparted excellent protection in both acidic media (S. A. Ali, A. J. Hamdan, A. A. Al-Taq, S. M. J. Zaidi, M. T. Saeed, In search of a functionality for an efficient inhibition of mild steel corrosion both in HCl and $H_2SO_4$, Corros. Eng. Sci. Technol. 46 (7) (2011) 796-806—incorporated herein by reference in its entirety). The mechanisms through which the corrosion inhibitors function have been ascribed to adsorption processes on either or both the anodic or cathodic sites. The formation of a good protective film (coating) on the metal surface essentially requires an inhibitor molecule to have (1) a hydrophilic polar end (e.g. cationic group), (2) a long alkyl chain to form a hydrophobic barrier, and (3) functional group like alkyne or a cinnamyl moiety which can undergo H atom-initiated polymerization between the adsorbed inhibitor molecules (F. B. Growcock, W. W. Frenier, V. R. Lopp, Proc. 6th Eur. Symp. on 'Corrosion inhibitors', Ferrara, Ann. Univ. Ferrara, N. S., Sez V, Suppl. 7, 1185, 1980; D. Jayaperumal, S. Muralidharan, P. Subramanium, G. Venkatachari, S. Senthilvel, Propargyl alcohol as hydrochloric acid inhibitor for mild steel-temperature dependence of critical concentration, Anti-Corros. Methods Mater. 44 (1997) 265-268; F. B. Growcock, Inhibition of Steel Corrosion in HCl by Derivatives of Cinnamaldehyde: Part I. Corrosion Inhibition Model, Corrosion 45(12) (1989) 1003-1007—each incorporated herein by reference in its entirety). Many inhibitors undergo physisorption on the metal surface (S. Muralidharan, K. L. N. Phani, S. Pitchumani, S. Ravichandran, S. V. K. Iyer, Polyamino-Benzoquinone Polymers: A New Class of Corrosion Inhibitors for Mild Steel, J. Electrochem. Soc. 142 (1995) 1478-1483—incorporated herein by reference in its entirety), while inhibitors having non-bonded and π-electrons may undergo chemisorption (N. Hackerman, R. M. Hurd, Proc. Int. Cong. on 'Metallic corrosion', London, Butterworth, (1962) 166-170—incorporated herein by reference in its entirety).

The $CO_2$ corrosion is explained using the reactions described in Reactions 10-16 below. It is the carbonic acid (not the dry $CO_2$) which, at the same pH, has been found to be more aggressive than hydrochloric acid for attacks to mild steel pipelines as a result of Reactions 12-16 shown below (G. Zhang, C. Chen, M. Lu, C. Chai, Y. Wu, Evaluation of inhibition efficiency of an imidazoline derivative in $CO_2$-containing aqueous solution, Mater. Chem. Phys. 105 (2007) 331-340; U. Lotz, L. Van Bodegom, C. Ouwehand, The effect of type of oil or gas condensate on carbonic acid corrosion, Corrosion 47 (1991) 635-644; K. Chokshi, W. Sun, S. Nesic, Iron carbonate scale growth and the effect of inhibition in $CO_2$ corrosion of mild steel, NACE International Corrosion Conference & Expo, Paper No. 05285, 2005—each incorporated by reference in its entirety):

  (Reaction 10)

  (Reaction 11)

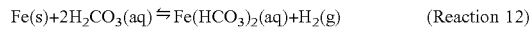  (Reaction 12)

  (Reaction 13)

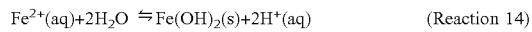  (Reaction 14)

  (Reaction 15)

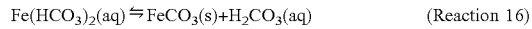  (Reaction 16)

Corrosion inhibitors bearing hetero-atoms of N, O, P, or S having non-bonded electrons and long chain hydrophobes are used when the formation of a protective ($FeCO_3$) layer (F. Farelas, M. Galicia, B. Brown, N. Nesic, H. Castaneda, Evolution of dissolution processes at the interface of carbon steel corroding in a $CO_2$ environment studied by EIS, Corros. Sci. 52 (2010) 509-517; K. Videm, A. Dugstad, Corrosion of carbon-steel in an aqueous carbon-dioxide environment. Part 1: solution effects, Mater. Performance 28 (1989) 63-67—each incorporated herein by reference in its entirety), which helps reduce the corrosive attack, is not favorable (Y. J. Tan, S. Bailey, B. B. Kinsella, An investigation of the formation and destruction of corrosion inhibitor films using electrochemical impedance spectroscopy (EIS), Corros. Sci. 38 (1996) 1545-1561; V. Jovancicevic, S. Ramachandran, P. Prince, Inhibition of carbon dioxide corrosion of mild steel by imidazolines and their precursors, Corrosion 55 (1999) 449-455; F. Bentiss, M. Triasnel, H. Vezin, M. Lagrenee, Linear resistance model of the inhibition mechanism of steel in HCl by triazole and oxadiazole derivatives: Structure-activity correlations, Corros. Sci. 45 (2003) 371-380—each incorporated herein by reference in its entirety). $FeCO_3$ is less soluble at high temperatures and pH values; as such higher temperatures usually decrease the corrosion rate because of formation of the more stable surface films (S. L. Wu, Z. D. Cui, F. He, Z. Q. Bai, S. L. Zhu, X. J. Yang, Characterization of the surface film formed from carbon dioxide corrosion on N80 steel, Mater. Lett. 58 (2004) 1076-1081; E. W. J. van Hunnik, B. F. M. Pots, E. L. J. A. Hendriksen, The Formation of protective $FeCO_3$: Corrosion Product Layers in $CO_2$ Corrosion, Corrosion/96, Paper No. 6, NACE, Houston, Tex., 1996; S. Nesic, K. L. J. Lee, A mechanistic model for carbon dioxide corrosion of mild steel in the presence of protective iron carbonate films-part 3: film growth model, Corrosion 59 (2003) 616-627—each incorporated herein by reference in its entirety). Electron-rich imidazolines are extensively used to minimize corrosion in the oil and gas industry (X. Liu, S. Chen, H. Ma, G. Liu, L. Shen, Protection of iron corrosion by stearic acid and stearic imidazoline self-assembled monolayers, Appl. Surf. Sci. 253 (2006) 814-820; X. Liu, P. C. Okafor, Y. G. Zheng, The inhibition of $CO_2$ corrosion of N80 mild steel in single liquid phase and liquid/particle two-phase flow by amino ethyl imidazoline derivatives, Corros. Sci. 51 (2009) 744-751; P. C. Okafor, X. Liu, Y. G. Zheng, Corrosion inhibition of mild steel by ethylamino imidazoline derivative in $CO_2$-saturated solution, Corros. Sci. 51 (2009) 761-768; F. Farelas, A. Ramirez, Carbon dioxide corrosion inhibition of carbon steels through bis-imidazoline and imidazoline compounds studied by EIS, Int. J. Electrochem. Sci. 5 (2010) 797-814; X. Liu, Y. G. Zheng, Effect of hydrophilic group on inhibition behaviour of imidazoline for $CO_2$ corrosion of N80 in 3% NaCl solution, Corros. Eng. Sci. Tech. 43 (2008) 87-92; M. W. S. Jawich, G. A. Oweimreen, S. A.

Ali, Heptadecyl-tailed mono- and bis-imidazolines: A study of the newly synthesized compounds on the inhibition of mild steel corrosion in a carbon dioxide-saturated saline medium" Corros. Sci. 65 (2012) 104-112—each incorporated herein by reference in its entirety).

Inadequate unraveling of the complex mechanism of $CO_2$ corrosion has become the impediment in the design of new inhibitors (A. Edwards, C. Osborne, S. Webster, D. Klenerman, M. Joseph, P. Ostovar, M. Doyle, Mechanistic studies of the corrosion inhibitor oleic imidazoline, Corros. Sci. 36 (1994) 315-325; G. McIntire, J. Lippert, J. Yudelson, The effect of dissolved CO2 and O2 on the corrosion of iron, Corrosion 46 (1990) 91-95—each incorporated herein by reference in its entirety). The effective commercial formulations used in the corrosion inhibition of oil field steel are mixtures of surface-active compounds: N-containing compounds, acetylenic compounds, surfactants, and aldehydes. Accordingly, in order to help alleviate economic loss as a result of mild steel corrosion, it will be desirable to design corrosion inhibitor compounds that combine the important functional features such as cationic charges, hydrophobic environment, alkyne, and cinnamyl motifs.

BRIEF SUMMARY OF THE INVENTION

The foregoing paragraphs have been provided by way of general introduction, and are not intended to limit the scope of the following claims. The described embodiments, together with further advantages, will be best understood by reference to the following detailed description taken in conjunction with the accompanying drawings.

In a first aspect, the present invention relates to a compound for inhibiting corrosion of mild steel having the following Formulas I or II:

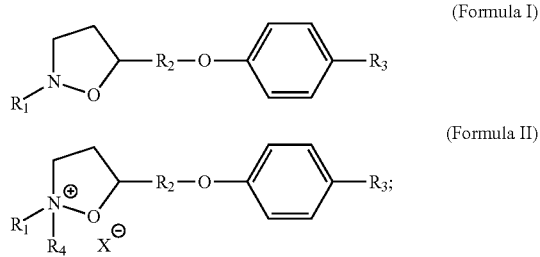

(Formula I)

(Formula II)

where $R_1$ is selected from hydrogen, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkyl, and substituted or unsubstituted heterocycloalkyl, preferably —$CH_3$, —$CH_2CH_3$. $R_2$ is selected from substituted or unsubstituted, branched or linear, $C_{1-22}$ alkyl, substituted or unsubstituted $C_{1-22}$ haloalkyl, substituted or unsubstituted $C_{2-22}$ alkenyl and substituted or unsubstituted $C_{2-22}$ alkynyl. $R_3$ is selected from substituted or unsubstituted $C_{1-12}$ aldehyde, substituted or unsubstituted acrylic acid, substituted or unsubstituted propanol and substituted or unsubstituted propenal. $R_4$ is selected from substituted or unsubstituted, branched or linear, $C_{2-22}$ alkynyl. X is selected from fluoride, chloride, bromide and iodide. Preferred embodiments of the compound is selected from p-9-(2-methylisoxazolidin-5-yl)undec-1-yloxybenzaldehyde, p-9-(2-methylisoxazolidin-5-yl)non-1-yloxycinnamaldehyde and p-9-[2-methyl-2-(2-popyn-1-yl) isoxazolidinium-5-yl]non-1-yloxycinnamaldehyde chloride.

The compound may be prepared with a method comprising the steps of alkylating an arylaldehyde with a haloalkene to form a haloaryl alkene and cycloadding a nitrone to the haloaryl alkene to form an isoxazolidine. In some embodiments, the method may further comprise the steps of contacting isoxazolidine with an acid to form an acid derivative and reducing then oxidizing the acid derivative to form a substituted cinnamaldehyde. In some embodiments, the method may even further comprise the step of quaternizing the nitrogen atom in the substituted cinnamaldehyde with a haloalkyne to form a quaternary salt.

In one embodiment, the compound is effective in inhibiting corrosion of mild steel surrounded by an environment containing at least one acidic fluid, at least one neutral salt or combinations thereof. In one embodiment, the acidic fluid is present at a saturated concentration.

In a preferred embodiment, the compound is effective in inhibiting corrosion of mild steel at concentrations of 10 to 1000 parts by the total weight of fluids that are in contact with the mild steel.

In a second aspect, the present invention relates to a composition for inhibiting corrosion of mild steel comprising a compound having Formulas I or II. Preferred embodiments of the compound is selected from p-9-(2-methylisoxazolidin-5-yl)undec-1-yloxybenzaldehyde, p-9-(2-methylisoxazolidin-5-yl)non-1-yloxycinnamaldehyde and p-9-[2-methyl-2-(2-popyn-1-yl) isoxazolidinium-5-yl]non-1-yloxycinnamaldehyde chloride.

In a third aspect, the present invention relates to a method of inhibiting the corrosion of mild steel, comprising contacting the mild steel with a composition comprising a compound Formulas I or II. In some embodiments, the compound in the composition is p-9-(2-methylisoxazolidin-5-yl)undec-1-yloxybenzaldehyde, p-9-(2-methylisoxazolidin-5-yl)non-1-yloxycinnamaldehyde or p-9-[2-methyl-2-(2-popyn-1-yl) isoxazolidinium-5-yl]non-1-yloxycinnamaldehyde chloride.

In one preferred embodiment, the mild steel in the method is contacted with the composition at high temperatures and high pressures that are similar to conditions in oil and gas wells.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
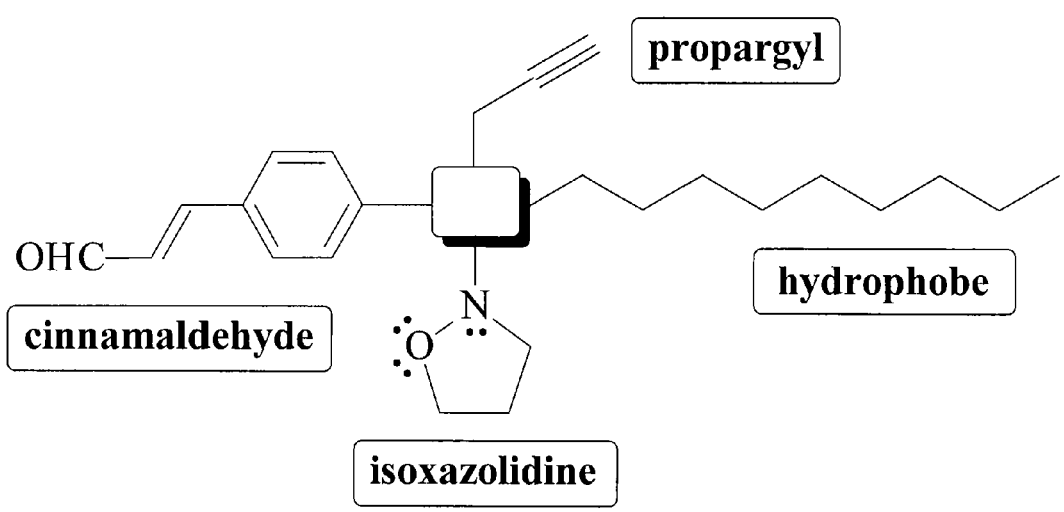
FIG. 1 illustrates the design of a corrosion inhibitor embedding cinnamaldehyde, propargyl, isoxazolidine and hydrophobic hydrocarbon chain structural motifs in a single molecular framework.

Referring now to the drawings, wherein like reference numerals designate identical or corresponding parts throughout the several views.

The present invention relates to novel compounds as inhibitors of mild steel corrosion and methods of synthesizing and characterizing thereof. Preferably, these compounds contain all or at least a substantial combination of structural and functional motifs such as cinnamaldehyde, isoxazolidine, alkyne (e.g. propargyl) and hydrophobe (e.g. a long, aliphatic hydrocarbon chain) as shown in FIG. 1 and the following Formulas I and II:

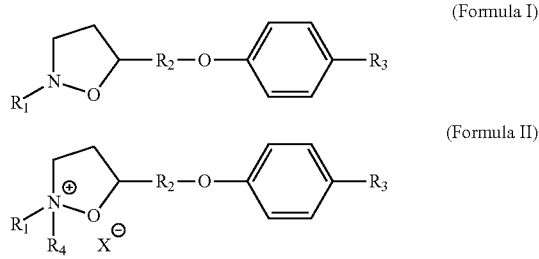

(Formula I)

(Formula II)

where $R_1$ is selected from hydrogen, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkyl, and substituted or unsubstituted heterocycloalkyl, preferably —$CH_3$, —$CH_2CH_3$. $R_2$ is selected from substituted or unsubstituted, branched or linear, $C_{1-22}$ alkyl, substituted or unsubstituted $C_{1-22}$ haloalkyl, substituted or unsubstituted $C_{2-22}$ alkenyl and substituted or unsubstituted $C_{2-22}$ alkynyl. $R_3$ is selected from substituted or unsubstituted $C_{1-12}$ aldehyde, substituted or unsubstituted acrylic acid, substituted or unsubstituted propanol and substituted or unsubstituted propenal. $R_4$ is selected from substituted or unsubstituted, branched or linear, $C_{2-22}$ alkynyl. X is selected from fluoride, chloride, bromide and iodide.

Examples of the inhibitor compounds may include p-9-(2-methylisoxazolidin-5-yl)undec-1-yloxybenzaldehyde (Formula III), p-9-(2-methylisoxazolidin-5-yl)non-1-yloxycinnamaldehyde (Formula IV) and p-9-[2-methyl-2-(2-popyn-1-yl) isoxazolidinium-5-yl]non-1-yloxycinnamaldehyde chloride (Formula V) with their chemical structures shown below:

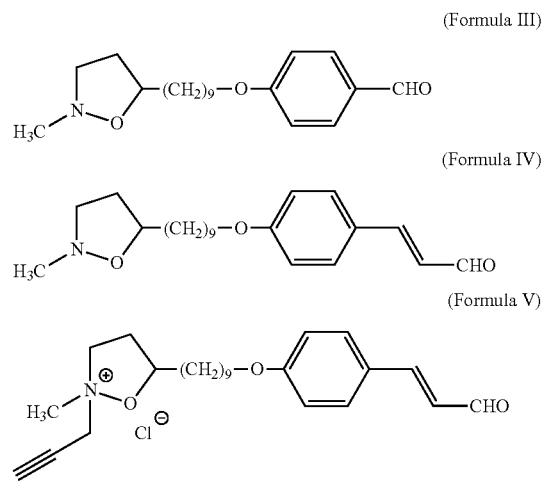

In some embodiments, inhibitor compounds described herein may be quaternary compounds. Quaternary compounds are cations consisting of a central positively nitrogen group atom with four substituents, especially organic (alkyl and aryl) groups, discounting hydrogen atoms.

In some embodiments, inhibitor compounds may be precursors or intermediate compounds of another inhibitor compound during organic synthesis. Inhibitor compounds of the present invention may be synthesized in a process with exemplary steps such as 1) alkylation of aldehyde and cycloaddition of alkene from the nitrone-alkene cycloaddition protocol; 2) condensation, reduction and oxidation of isoxazolidine; and 3) quaternization.

Steel is an alloy of iron and carbon. Mild steel, according to the present invention, is a low-carbon steel wherein the carbon content is no greater than 0.29%. In some embodiments, the carbon content of mild steel is 0.05-0.29%, preferably 0.16-0.29%. Objects that are made of mild steel include but are not limited to pipelines in the oil and gas industry, water pipelines, transportation vehicles.

For purposes of the present invention, a "corrosion inhibitor" or an "inhibitor" refers to a substance, compound or composition, when added in a small concentration to an environment, reduces the corrosion rate of a metal or an alloy exposed to that environment. Inhibitors often play an important role in the oil extraction and processing industries where they have always been considered to be the first line of defense against corrosion. Anodic inhibitors are inhibitors that usually act by forming a protective oxide film on the surface of the metal or alloy, therefore causing a large anodic shift of the corrosion potential ($E_{corr}$). The shift forces the metallic surface into the passivation region, which is why anodic inhibitors are sometimes referred to as passivators. Cathodic inhibitors act by either slowing the cathodic reaction itself or selectively precipitating on cathodic areas to limit the diffusion of reducing species to the surface. There are also mixed inhibitors that work by reducing both the cathodic and anodic reactions. They are typically film forming compounds that cause the formation of precipitates on the surface blocking both anodic and cathodic sites indirectly.

In one embodiment, compounds described herein are anodic inhibitors that cause a shift of the corrosion potential ($E_{corr}$) in the positive direction of at least 50 mV, preferably 85-100 mV. In another embodiment, the compounds are mixed inhibitors.

For purposes of the present invention, "parts per million" or "ppm" refers to an expression of concentration by mass or weight. For example, 1 ppm of a corrosion inhibitor compound denotes 1 part of the corrosion inhibitor per 1,000,000 or $10^6$ parts, wherein $10^6$ parts is the total weight of fluids (e.g. liquids, gases or combinations thereof) that are in contact with the mild steel that is to be protected. Alternatively, 1 ppm of a corrosion inhibitor denotes 1 part of the corrosion inhibitor per the total weight of fluids that are contained or carried in a mild steel pipeline or an oil/gas well made of mild steel.

Inhibitor compounds according to the present invention are effective in protecting mild steel against corrosion in various environments such as acidic and high salt concentration environments. Acidic agents may be in liquid or gas forms and include acids such as HCl, $H_2SO_4$, $HNO_3$ and gases such as $CO_2$ and $H_2S$. These acidic agents may be present in a corrosive environment in saturated concentrations, or in a concentration range of 0.1 M to 10 M. Neutral salts such as NaCl have been known to cause serious corrosion to mild steel, and may be present in an environment at 0.05 M to 2 M, or 0.1 M to 1 M, or about 0.5 M. In some embodiments, saline may also be present in the environment.

In some embodiments, the inhibitor compounds act as adsorbents and may employ both physisorption and chemisorption mechanisms when they are in contact with mild steel. The chemisorption process wherein nucleophilic electrons are donated to the surface of mild steel are facilitated by the non-bonded and π-electrons of the isoxazolidine, aromatic and hydrophobic tail moieties in the inhibitor compounds These electron-rich moieties help the compounds to form strong electronic bonds with the metallic surface. Phyisorption takes place when the compounds adhere to the metal surface (the adsorbent) and form a protective film of the adsorbate. The alkyne moiety gives the inhibitor compounds the physiorption abilities.

The present invention is also directed at methods of inhibiting corrosion of mild steel with the compounds disclosed herein. In general, inhibitor compounds are added to the fluids that surround mild steel or an object made of mild steel, for example, fluids that are routinely carried in a mild steel pipeline. These fluids contain at least one of the acidic agents and salts previously described and therefore create a corrosive environment for mild steel.

In some embodiments, these methods are implemented when the object made of mild steel is not in use. For example, inhibitor compounds may be dissolved in a treatment fluid for mild steel pipelines, oil and gas wells at concentrations such as 10-1000 ppm, preferably 25-500 ppm, or 100-400 ppm. In another embodiment, objects made of mild steel may be immersed in a treatment fluid containing the inhibitor compounds at concentrations described above.

At low concentrations of inhibitor compounds such as concentrations described above, the inhibition efficiency directly correlates with the surface coverage of the electrode by an inhibitor molecule at its lower concentration, i.e. η %=θ %. Corrosion inhibition efficiencies may be measured with the Tafel extrapolation, linear polarization resistance (LPR), gravimetric or other similar methods. Inhibitor compounds described herein achieve corrosion inhibition efficiencies (η %) of at least 70%, preferably at least 85%, for example, 95.0-99.5% in HCl, 90-98% in $H_2SO_4$ and 95-99% in $NaCl/CO_2$.

Preferably, for applications in the oil and gas industry, the corrosion inhibitors of the present invention are stable at high temperatures and high pressures. Oil and gas wells can reach temperatures higher than 140° C., (e.g. 150-160° C.) and pressures of up to 1,000 bar (e.g. 700-800 bar).

Additionally, the present invention relates to compositions for inhibiting corrosion of mild steel comprising compounds disclosed herein. Other additives of the composition include demulsifiers, water wetting agents, surfactants, viscosifiers, commingled gases, defoamers, other corrosion inhibitors such as polymeric materials and salts, organic and inorganic acids, iron control agents, sequestering and/or chelating agents, phosphates, quaternaries and amine salts.

The examples below are intended to further illustrate protocols for preparing the compounds and characterizing them for mild steel corrosion inhibitory efficiency described herein, and are not intended to limit the scope of the claims.

Example 1

Materials and Reagents

Paraformaldehyde, 10-undecenyl bromide, propargyl chloride, p-hydroxybenzaldehyde, and N-methylhydroxyamine hydrochloride, malonic acid, manganese dioxide, piperidine, silica gel 100, obtained from Fluka Chemie AG, were used as received. Sodium chloride of >99.5 purity from Baker Chemical Company was used for the inhibition analysis.

Corrosion study by gravimetric and electrochemical methods were carried out with mild steel coupons of the following composition: 0.089% (C), 0.037 (Cr), 0.34% (Mn), 0.022 (Ni), 0.010 (P), 0.007 (Mo), 0.005 (V), 0.005 (Cu), 99.47% (Fe). For the electrochemical tests, a 1 mm thick mild steel sheet was machined to a flag shape with an approximate stem of 3 cm. Insulating the stem by araldite (affixing material) provided 2 cm² exposed area which was abraded with increasing grades of emery papers (100, 400, 600 and 1500 grit size), washed with deionized water, acetone and followed by oven drying at 110° C. For the gravimetric test, the mild steel coupons were cleaned as described above. The dried specimens were stored in a desiccator. Before their use, the electrode specimens were placed in an ultrasonic bath for 5 min, washed with distilled water and used immediately.

For autoclave tests the two types of mild steel coupons (Coupon A and Coupon B) have the following compositions:

Coupon A: 0.082% (C), 0.016% (Cr), 0.207% (Mn), 0.062% (Ni), 0.029% (Cu), 0.012% (Mo), <0.001% (V), 0.032% (Si), <0.0005% (P), 0.0059% (S), 0.011% (Co), 0.045% (Al), <0.0010% (Nb), <0.0005% (Ti), <99.3% (Fe).

Coupon B: 0.168% (C), 0.038% (Cr), 0.495% (Mn), 0.034% (Ni), 0.074% (Cu), 0.0081% (Mo), 0.001% (V), 0.237% (Si), 0.014% (P), 0.024% (S), 0.011% (Co), 0.080% (Al), 0.0019 (Nb), 0.0015% (Ti), <98.6% (Fe).

Reagent A. C. S. HCl and $H_2SO_4$ (Fisher Scientific Company) and distilled deionized water were used to prepare 1, 4 and 7.7 M HCl and 0.5 M $H_2SO_4$ solutions. Corrosion inhibition tests were performed in 0.5 M NaCl in the presence of $CO_2$ (1 atm) at 40° C. as well as at higher pressure (10 bar) of $CO_2$ and temperature of 120° C. Each solution was de-aerated with 99.999% $N_2$ (30 min) and then continuously saturated with 99.999% pure $CO_2$. The high purity $CO_2$ was used to avoid corrosion by oxygen. Studies using $CO_2$ gas showed that the corrosion at pH<4 is mainly by reaction with $H^+$, while the active species in less acidic solutions adsorbed $CO_2$ or $H_2CO_3$ (K. Videm, A. Dugstad, Corrosion of carbon-steel in an aqueous carbon-dioxide environment. Part 1: solution effects, Mater. Performance 28 (1989) 63-67—incorporated herein by reference in its entirety). To avoid possible changes in the mechanism of the corrosion reaction, a solution of $NaHCO_3$ (100 mg/L) was used to maintain a pH between 5.0 and 5.5.

Example 2

Physical Characterization Methods

Potentiostat (Model 283, EG&G PARC) was used for the electrochemical measurements. R&D Autoclave Bolted Closure System (Model #401C-0679 from Autoclave Engineers), Control System interfaced with Computer, and PC with monitor (High Tech Engineering, India) has been installed for the study of corrosion inhibition under higher temperature and pressure.

The IR spectra were recorded on a Perkin Elmer 16F PC FTIR spectrometer, and the $^1H$ and $^{13}C$ NMR spectra were measured in $CDCl_3$ using TMS as internal standard on a JEOL LA 500 MHz NMR spectrometer. Elemental analyses were carried out on a Carlo-Erba Elemental Analyzer Model 1106.

Example 3

Synthesis of Corrosion Inhibitors

Figure 2:
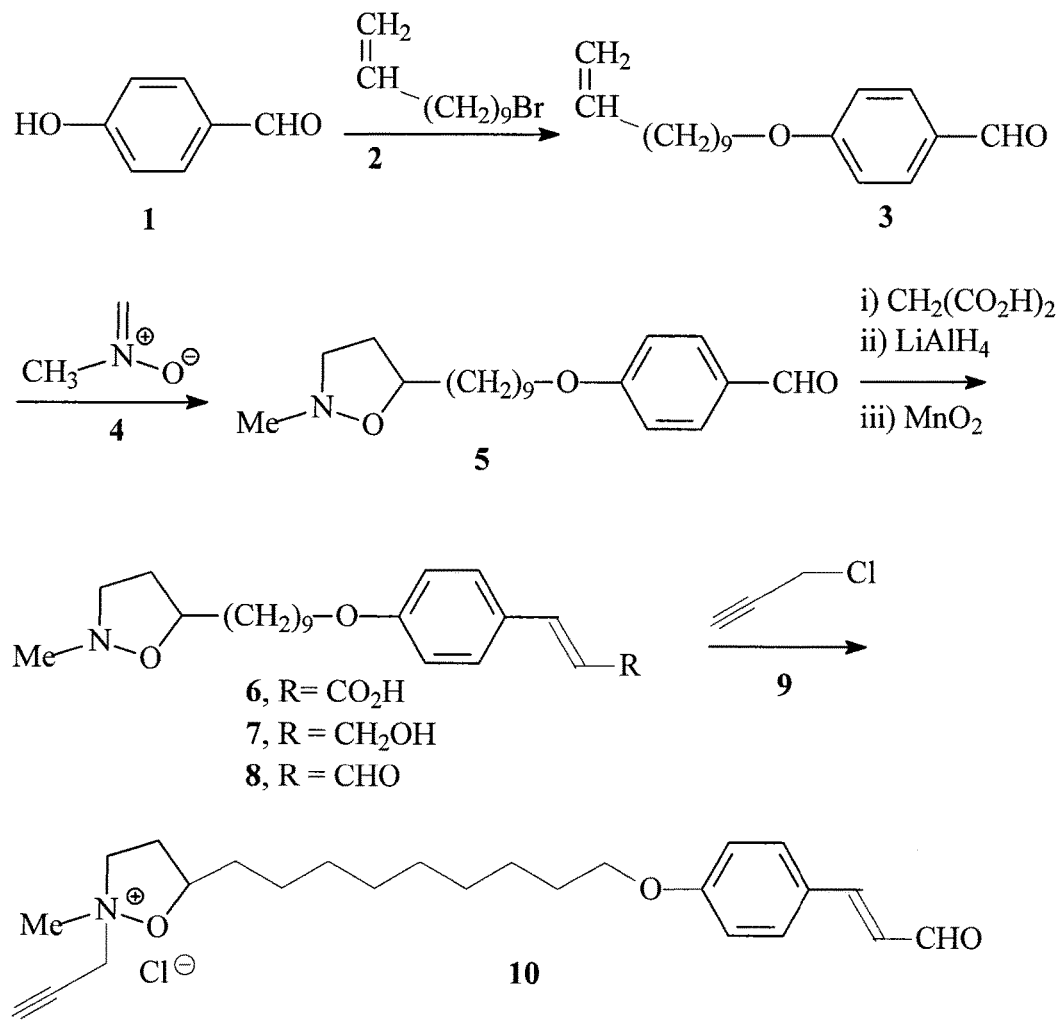
FIG. 2 is a schematic diagram illustrating the organic synthesis of corrosion inhibitor molecules according to the present invention.
Figure 2:
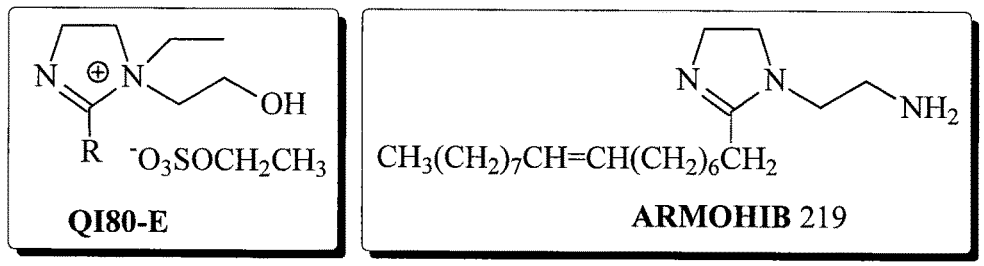
Figure 3:
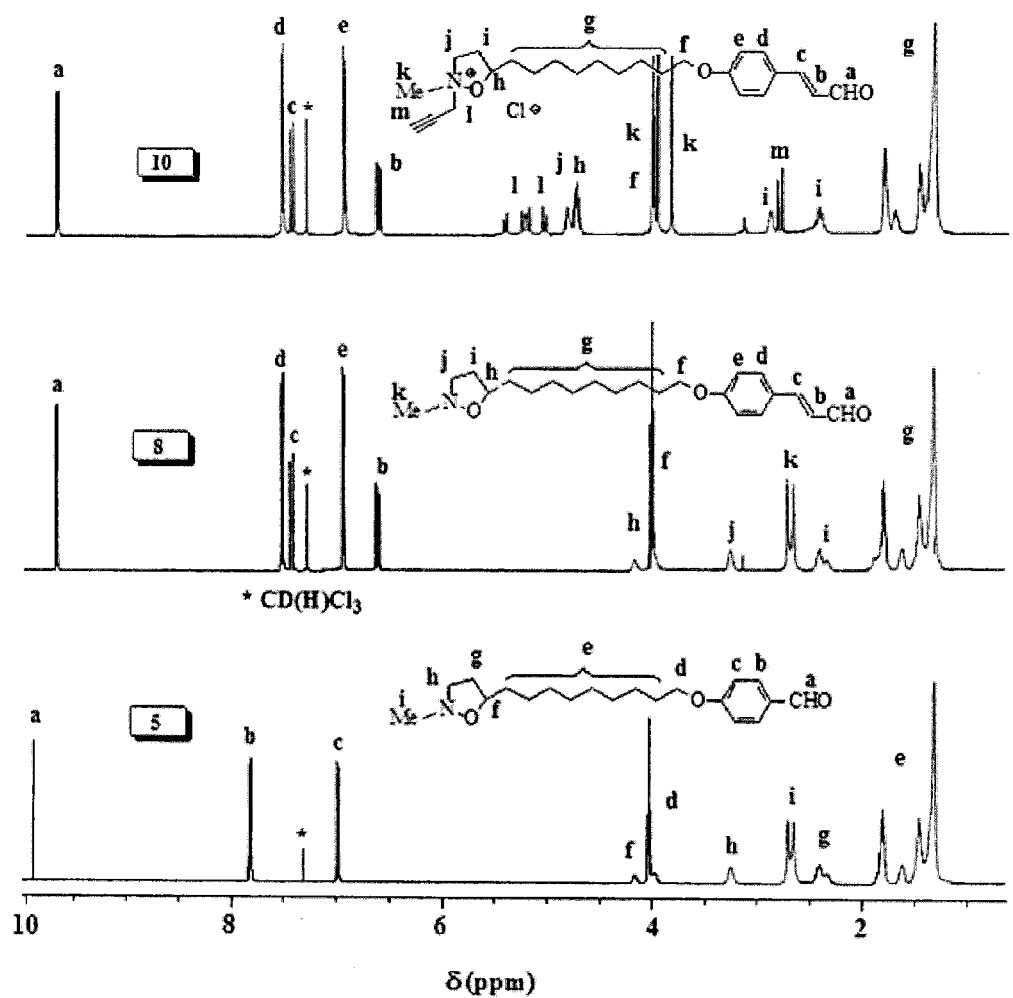
FIG. 3 illustrates $^1H$ NMR spectra of compounds 5, 8 and 10 in $CDCl_3$.
Figure 4:
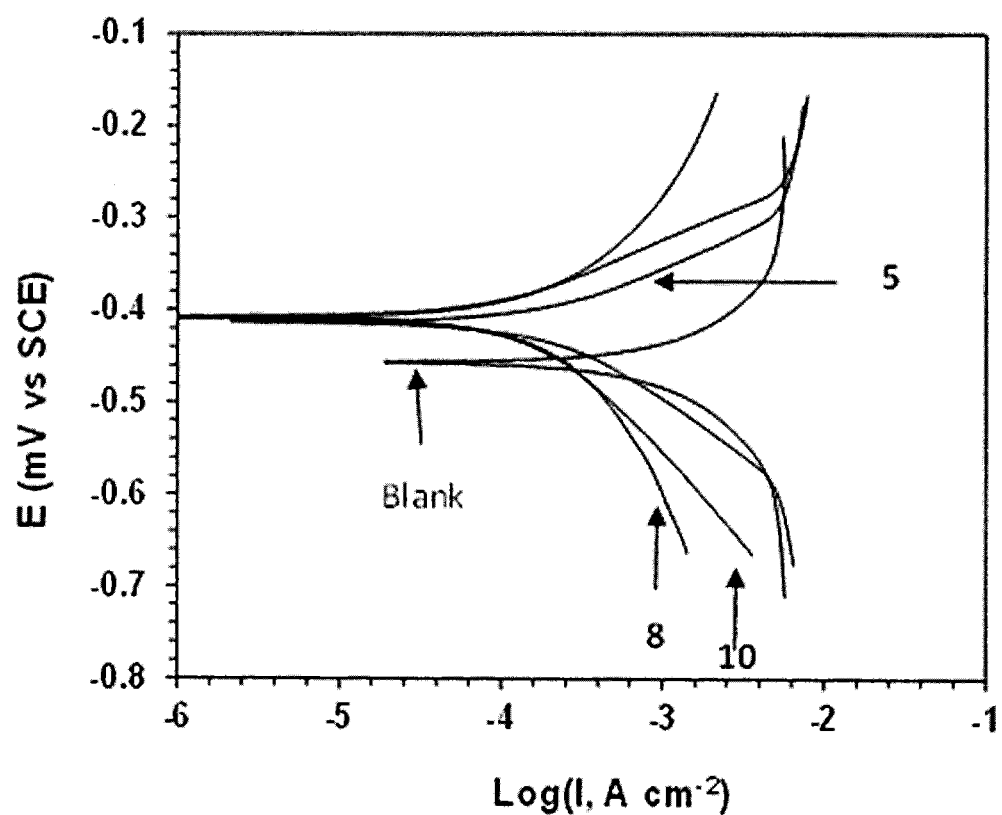
FIG. 4 shows potentiodynamic polarization curves at 60° C. for mild steel in 1 M HCl containing 100 ppm of compounds 5, 8 or 10.
Figure 5A:
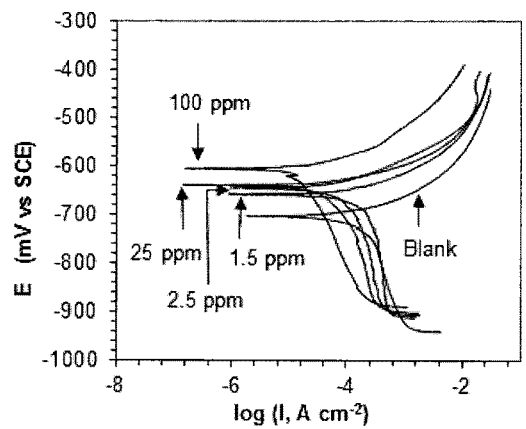
FIG. 5a shows potentiodynamic polarization curves at 40° C. for mild steel in $CO_2$ saturated 0.5 M NaCl containing different concentrations of compound 5.
Figure 5B:
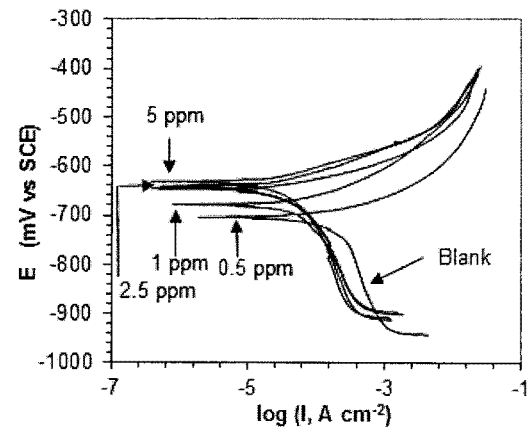
FIG. 5b shows potentiodynamic polarization curves at 40° C. for mild steel in $CO_2$ saturated 0.5 M NaCl containing different concentrations of compound 8.
Figure 5C:
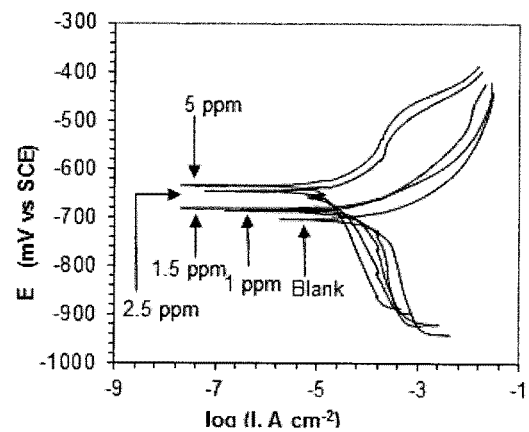
FIG. 5c shows potentiodynamic polarization curves at 40° C. for mild steel in $CO_2$ saturated 0.5 M NaCl containing different concentrations of compound 10.
Figure 5D:
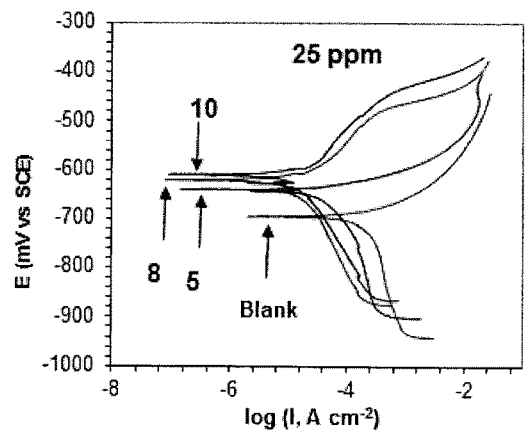
FIG. 5d shows potentiodynamic polarization curves at 40° C. for mild steel in $CO_2$ saturated 0.5 M NaCl containing 25 ppm of compounds 5, 8 or 10.

Referring to FIG. 2, the synthesis of the inhibitor molecules was achieved using nitrone-alkene cycloaddition protocol (J. J. Tufariello in "1,3-dipolar Cycloaddition Chemistry" ed. A. Padwa, Wiley-Interscience, New York, 1984; P. N. Confalone, E. E. Huie, The (3+2) Nitrone-Olefin Cycloaddition Reaction, Organic Reactions 36 (1988) 1-173—each incorporated herein by reference in its entirety). The nitrone-cycloaddition reactions are often used as a key step in the synthesis of many biologically important natural products (H. Ida, C. Kibyasi, Natural product using nitrones cycloaddition reaction, Yuki Gosei, Kagaku Kyokaishi, 41 (1983) 652-666—incorporated herein by reference in its entirety). The specialty alkene p-undec-10-enyloxybenzaldehyde (compound 3) bearing an aromatic aldehyde motif at the terminal of a hydrophobic alkyloxy chain was prepared via alkylation of p-hydroxybenzaldehyde (compound 1) with 11-bromo-1-undecene (compound 2). The cycloaddition of nitrone (compound 4) with p-undec-10-enyloxybenzaldehyde then gave p-9-(2-methylisoxazolidin-5-yl)undec-1-yloxybenzaldehyde (compound 5), an isoxazolidine, in an excellent yield. The Knoevenagel condensation of compound 5 with malonic acid gave p-9-(1-methylisoxazolidin-5-yl)non-1-yloxycinnamic acid (compound 6) in excellent yield. The p-9-(1-methylisoxazolidin-5-yl)non-1-yloxycinnamic acid, upon $LiAlH_4$ reduction followed by $MnO_2$ oxidation afforded p-9-(2-methylisoxazolidin-5-yl)non-1-yloxycinnamaldehyde (compound 8), a substituted cinnamaldehyde, which was then quaternized with propargyl chloride (compound 9) to give salt p-9-[2-methyl-2-(2-popyn-1-yl) isoxazolidinium-5-yl]non-1-yloxycinnamaldehyde chloride (compound 10) in quantitative yield. Hence, p-9-[2-methyl-2-(2-popyn-1-yl) isoxazolidinium-5-yl]non-1-yloxycinnamaldehyde chloride contains all of the four following functional motifs expected to impart corrosion inhibition: cinnamaldehyde skeleton (to minimize hydrogen embrittlement), quaternary nitrogen (to impart solubility), hydrophobic spacer $(CH_2)_9$ (for surface coverage), propargyl moiety (to produce polymeric film) as well as an electron-rich aromatic moiety (for π-electron donation) in a single molecule. The nitrogen in the isoxazolidine moiety is less basic ($pK_b$: ≈10.4) because of the adjacent electronegative oxygen but is more nucleophilic in comparison to a tertiary amine $R_3N$ ($pK_b$: ≈4.2), due to the former having three repulsive adjacent lone pairs in the :N-Ö: group (S. A. Ali, A. M. El-Shareef, R. F. Al-Ghamdi, M. T. Saeed, The isoxazolidines: the effects of steric factor and hydrophobic chain length on the corrosion inhibition of mild steel in acidic medium, Corros. Sci. 47 (2005) 2659-2678—incorporated herein by reference in its entirety). This was expected to make the isoxazolidine moiety in compounds 5 and 8 a potent motif for chemisorption by nucleophilic electron donation to the metal surface. The present invention also successfully assembled a rather water-insoluble cinnamaldehyde moiety with the isoxazolidine ring where the unquenched valency of nitrogen can be manipulated to protonated $R^1R^2NH^+$ or $R^1R^2N^+CO_2^-$ (in the presence of $CO_2$) (as in compounds 5 and 8) or quaternary salt (compound 10) so as to impart overall water-solubility. The $^1H$ NMR spectra of these compounds 5, 8 and 10 are shown in FIG. 3. Spectral analyses supported the assigned structure of the cycloaddition products. Each of compounds 5 and 8 is a mixture of two conformationally mobile invertomers of cis- and trans-disposed substituents at 2,5 positions; and the spectrum of compound 10 reveals the presence of two isomeric salts of E and Z disposition of the 2,5-substituents. To the knowledge of the applicants, it is the first time a cinnamaldehyde moiety is incorporated in a nitrone cycloaddition product (compounds 8 or 10).

Two commercial inhibitor samples QI80-E, an ethylsulfate of quaternized imidazolines (mixture having $R=C_{12}$ to $C_{22}$) from Materials Performance, and ARMOHIB 219 from AKZO NOBEL were tested for comparison of corrosion inhibitory efficiencies. The chemical structures of these two commercially available inhibitors are shown in FIG. 2.

Each reaction step involved in the synthesis of compounds 5, 8 and 10, including the intermediates, is described in detail in the following Examples 4-9.

Example 4

Synthesis of p-undec-10-enyloxybenzaldehyde

To a stirring solution of sodium ethoxide (0.065 mol; prepared by adding 1.5 g sodium in ethanol (30 cm$^3$) was added p-hydroxybenzaldehyde (compound 1 in FIG. 2, 7.95 g, 0.065 mmol) at 20° C. After the mixture became homogeneous (ca. 5 min), 11-bromo-1-undecene (compound 2 in FIG. 2, 15.2 g, 0.065 mol) was added and the mixture was heated at 65° C. for 12 h and at 90° C. for a further period of 12 h. The concentrated residue in ether (50 cm$^3$) was washed with water (2×100 cm$^3$), 5% NaOH solution (2×50 cm$^3$), followed again by water (2×50 cm$^3$). The organic layer was dried and concentrated to give p-undec-10-enyloxybenzaldehyde (compound 3 in FIG. 2, 18.7 g, 88.7%) as a brown liquid. $^1H$ NMR spectrum revealed the product as very pure, and as such used without further purification.

Example 5

Synthesis of adduct p-9-(2-methylisoxazolidin-5-yl) undec-1-yloxybenzaldehyde

To a mixture of N-methylhydroxylamine hydrochloride (5.00 g, 60 mmol) in ethanol (45 cm$^3$) was added sodium acetate-trihydrate (8.84 g, 65 mmol) followed by paraformaldehyde (2.7 g, 90 mmol). After stirring at 65° C. for 40 min to generate nitrone (compound 4 in FIG. 2, alkene (compound 3 in FIG. 2, 17.3 g, 63 mmol) was added, and the reaction mixture in a pressure-vessel was then heated at 100° C. for 8 h. Ethanol was removed and water (50 cm$^3$) was added to the residue, and solid NaHCO$_3$ was added to neutralize the solution. The aqueous layer was extracted with ether (3×75 cm$^3$). The ether solution was dried, concentrated, and the crude product upon chromatographic purification using ether as the eluent gave adduct p-9-(2-methylisoxazolidin-5-yl)undec-1-yloxybenzaldehyde (compound 5 in FIG. 2, white solid, 18.9 g, 90%). Melting point: 52-53° C. (ether-hexane).

Example 6

Synthesis of p-9-(1-methylisoxazolidin-5-yl)non-1-yloxycinnamic acid

A solution of the p-9-(2-methylisoxazolidin-5-yl)undec-1-yloxybenzaldehyde (compound 5 of FIG. 2, 6.67 g, 20 mmol), malonic acid (2.5 g, 24 mmol), piperidine (200 mg) in pyridine (20 cm$^3$) was heated to 120° C. for 4 h. The solvent pyridine was removed, and the residual liquid upon silica gel chromatography using 95:5 CHCl$_3$/MeOH gave p-9-(1-methylisoxazolidin-5-yl)non-1-yloxycinnamic acid (compound 6 of FIG. 2, white solid, 6.83 g, 91%). Melting point: 113-114° C. (ether).

Example 7

Synthesis of p-9-(2-methylisoxazolidin-5-yl)non-1-yloxycinnamyl alcohol

To a solution of p-9-(1-methylisoxazolidin-5-yl)non-1-yloxycinnamic acid (compound 6 of FIG. 2, 5.00 g, 13.3 mmol) in ether (150 cm$^3$) at 0° C. was added LiAlH$_4$ (0.7 g, 18.4 mmol), and the mixture was stirred at 0° C. for 1 h and 20° C. for another hour. The reaction mixture was quenched by successive addition of water (0.7 cm$^3$), 10% NaOH solution (0.7 cm$^3$) and water (2.8 cm$^3$). The white solid was washed with ether. The removal of ether afforded the p-9-(2-methylisoxazolidin-5-yl)non-1-yloxycinnamyl alcohol as a white solid (compound 7 of FIG. 2, 4.1 g, 85%). Melting point: 64-65° C. (ether).

Example 8

Synthesis of p-9-(2-methylisoxazolidin-5-yl)non-1-yloxycinnamaldehyde

A mixture of p-9-(2-methylisoxazolidin-5-yl)non-1-yloxycinnamyl alcohol (compound 7 of FIG. 2, 3.62 g, 10 mmol) in CH$_2$Cl$_2$ (150 cm$^3$) and MnO$_2$ (30 mmol) was stirred at 20° C. for 96 h. After filtration and concentration, the residual product was purified over silica gel chromatography using an eluent of 99:1 Et$_2$O-MeOH mixture to give p-9-(2-methylisoxazolidin-5-yl)non-1-yloxycinnamaldehyde as a white solid (compound 8 of FIG. 2, 2.7 g, 75%). Melting point: 60-61° C. (ether-pentane).

Example 9

Quaternization of p-9-(2-methylisoxazolidin-5-yl) non-1-yloxycinnamaldehyde with propargyl chloride: Synthesis of quaternary salt p-9-[2-methyl-2-(2-popyn-1-yl) isoxazolidinium-5-yl]non-1-yloxycinnamaldehyde chloride A solution of the p-9-(2-methylisoxazolidin-5-yl)non-1-yloxycinnamaldehyde (compound 8 of FIG. 2, 2.0 g, 5.56 mmol) and propargyl chloride (compound 9 of FIG. 2, 1.0 g, 13.4 mmol) in dry acetone (5 cm$^3$) was stirred at 20° C. for 24 h. The salt started precipitating out within an hour. The removal of the solvent followed by washing the residue with ether (2×10 cm$^3$) gave a pale yellow solid of the quaternary salt p-9-[2-methyl-2-(2-popyn-1-yl) isoxazolidinium-5-yl]non-1-yloxycinnamaldehyde chloride (compound 10 of FIG. 2, 2.34 g, 97%).

Example 10

Gravimetric Measurements in 0.5 M NaCl Saturated with CO$_2$ (1 Atm) at 40° C., 1 M HCl, 4 M HCl, 7.7 M HCl and 0.5 M H$_2$SO$_4$ at 60° C.

For gravimetric measurements, the steel coupons measuring 2.5×2.0×0.1 cm$^3$ were used. Inhibitor efficiency at 40° C. for 7 days was determined by hanging the steel coupon measuring 2.5×2.0×0.1 cm$^3$ into a 0.5 M NaCl (150 cm$^3$) in the presence of CO$_2$ (1 atm) in the absence and presence of the inhibitors (200 ppm). At the end, the coupons were cleaned with distilled water, abraded lightly with emery paper, followed by washing with distilled water, acetone and drying at 110° C.

The inhibition study in 1 M HCl and 0.5 M H$_2$SO$_4$ was carried out as above using acid solutions of 250 cm$^3$ for an immersion time of 6 h. For studies conducted with 4 and 7.7 M HCl, a solution volume of 500 cm$^3$ was used.

The results of weight loss measurements at 60° C. after 6 h of immersion of coupons (in 1, 4, 7.7 M HCl and 0.5 M H$_2$SO$_4$) for the compounds 5, 6, 8, and 10 are reported in Tables 1 and 2. Percent inhibition efficiency (i %) was calculated using Equation 1:

$$\eta \% = \frac{\text{Weight loss (blank)} - \text{Weight loss (inhibitor)}}{\text{Weight loss (blank)}} \times 100 \quad \text{(Equation 1)}$$

Triplicate determinations were made for each experiment. Where the masses of the coupons differed, relative weight loss of the coupons were used to calculate the η % using Equation 2:

$$\eta \% = \frac{\Delta \overline{W}_o - \Delta W}{\Delta \overline{W}_o} \times 100 \quad \text{(Equation 2)}$$

where $\Delta \overline{W}_o$ and $\Delta W$ are the respective mean relative weight loss of the coupons in the blank and inhibitor solution. In Equations 3 and 4, $W_{ib}$ and $W_{fb}$, are the initial and final masses, respectively, of the coupons in blank solutions while $W_{is}$ and $W_{fs}$ represent the corresponding masses in the inhibition solution:

$$\Delta \overline{W}_o = [\Sigma(W_{ib} - W_{fb})/W_{ib}]3 \quad \text{(Equation 3)}$$

$$\Delta W (W_{is} - W_{fs})/W_{is} \quad \text{(Equation 4)}$$

The average η % reported in the Tables 1 and 2 is found to have a standard deviation of 0.3-3.5%.

TABLE 1

The η %[a] for different inhibitors for the inhibition of corrosion of mild steel exposed at 60° C. in 1M HCl for 6 h, 4M HCl for 3 h and 7.7M HCl for 2 h.

| Com- pound | η % at different concentrations of compounds (ppm) and HCl (M) | | | | | | | | |
|---|---|---|---|---|---|---|---|---|---|
| | 5 | 10 | 25 | 50 | 100 | 200 | 400 | 50 4M HCl | 50 7.7M HCl |
| | | | | 1M HCl | | | | | |
| 5[b] | 67.9[b] | 94.6 | 96.6 | 98.5 | 98.1 | 99.3 | 99.3 | 98.3 | 93.3 |
| 6[c] | 71.5 | 87.3 | 95.1 | 98.1 | 98.7 | 99.3 | 99.7 | 91.3 | 87.2 |
| 8 | 72.2 | 93.8 | 95.4 | 98.6 | 98.9 | 99.2 | 99.4 | 92.3 | 88.2 |
| 10[d] | 73.5 | 95.3 | 97.1 | 98.1 | 99.1 | 99.6 | 99.5 | 98.7 | 94.3 |

[a]IE (i.e. η) = surface coverage θ.
[b]3 ppm, η % 53.8; 1 ppm, η % 27.8; 0.5 ppm, η % 16.5.
[c]3 ppm, η % 58.3; 1 ppm, η % 33.3; 0.5 ppm, η % 21.4.
[d]3 ppm, η % 64.3, 1 ppm; η % 38.5; 0.5 ppm, η % 27.3.

As can be seen in Table 1, inhibition efficiencies (η %) of ~99% were achieved in the presence of 50 ppm of inhibitor molecules (compounds 5, 6, 8 or 10). Increasing the inhibitor concentration increased the η % to a limiting value which indicated the formation of a monolayer film on the metal coupon. At an inhibitor concentration of 50 ppm, the effect of HCl strength on the inhibition efficiency revealed that the inhibitors performed well in 4 M as well as in 7.7 M HCl. Compound 10 gave the best protection at a concentration of 50 ppm: η % of 98.1, 98.7 and 94.3 in 1 M, 4 M and 7.7 M HCl, respectively.

TABLE 2

The η % for different concentrations of inhibitors for the inhibition of corrosion of mild steel exposed at 60° C. in 0.5M $H_2SO_4$ for 6 h.

| Compound | η % at different concentrations of compounds (ppm) | | | | | | |
|---|---|---|---|---|---|---|---|
| | 5 | 10 | 25 | 50 | 100 | 200 | 400 |
| 5 | 19.7 | 31.8 | 44.7 | 59.7 | 76.1 | 87.3 | 93.6 |
| 8 | 26.6 | 43.0 | 57.9 | 71.2 | 85.3 | 92.8 | 95.2 |
| 10 | 38.1 | 62.1 | 70.2 | 83.2 | 88.9 | 94.5 | 96.7 |

As can be seen in Table 2, the synthesized compounds 5, 8 and 10 showed good inhibition efficacies, achieving η % in the range 94-97% in the presence of 400 ppm of the inhibitor molecules. The literature does not document many compounds, which are equally effective in arresting mild steel corrosion both in HCl and in $H_2SO_4$ media.

The results of weight loss measurements at 40° C. after 7 days of immersion for the compounds in 0.5 M NaCl solution in the presence of $CO_2$ (1 atm) are reported in Table 3. Duplicate determinations were made with each of the solutions.

TABLE 3

Corrosion inhibition efficiency, η %, using polarization resistance, Tafel plots and gravimetric method of mild steel samples in various solutions containing 200 ppm of inhibitors in 0.5M NaCl/$CO_2$ (1 atm) at 40° C.

| | η % | | |
|---|---|---|---|
| Compound | Polarization method | Tafel method | Gravimetric method |
| 5 | 90.5 | 95.5 | 96 |
| 8 | 97.8 | 95.6 | 96 |
| 10 | 97.6 | 98.5 | 97.8 |

Example 11

Gravimetric Measurements at High Temperature and Pressure: Autoclave Experiments Experiments were carried out using autoclave with a capacity of 1,000 $cm^3$. The autoclave is equipped with temperature probe, pressure transducer, a spurger and a cooling coil. The autoclave is heated by an electrically heated jacket. A temperature probe inside the jacket measured the skin temperature of the autoclave. A feedback PID controller controlled the temperature inside the reactor. The temperature control and pressure read-out was done via a SCADA-HMI system specially designed for this application. The set-up through this system was attached to a microcomputer. In order to have a better control on the inside temperature, cooling water was used to reduce the temperature of the test solution.

Experiments were conducted at 10 bar and 120° C. in 0.5 M NaCl solution saturated with carbon dioxide to approximately simulate the conditions present in oil and gas field applications. The solution (50 $cm^3$) was poured into a glass beaker, which was kept in the autoclave. Carbon dioxide was bubbled for 20 min to ensure that all dissolved oxygen was knocked off the test solution. Subsequently, the carbon-steel coupons were immersed into the solution. The autoclave was closed using a torque wrench. After assembling the temperature and pressure sensors, the autoclave was pressurized to a desired level using carbon dioxide gas. A desired temperature was then set thru SCADA software. The system monitored the temperature and pressure through entire duration of the experiment for 48 h.

The results of the experiments carried out at temperature of 120° C. and a pressure of 10 bar $CO_2$ in 0.5 M NaCl for 48 h are given in Table 4. Duplicate determinations were made in each case.

TABLE 4

Corrosion rates and inhibition efficiencies of various corrosion inhibitors (200 ppm) at 120° C. and 10 bar pressure of $CO_2$ in 3% NaCl solution.

| Solution | Coupon[a] | % Inhibition | Average % Inhibition |
|---|---|---|---|
| Blank | A | — | — |
| | B | — | |
| 5 | A | 78.5 | 79.2 |
| | B | 79.8 | |
| 8 | A | 88.6 | 88.3 |
| | B | 87.9 | |
| 10 | A | 84.0 | 84.9 |
| | B | 85.7 | |

TABLE 4-continued

Corrosion rates and inhibition efficiencies of various corrosion inhibitors (200 ppm) at 120° C. and 10 bar pressure of $CO_2$ in 3% NaCl solution.

| Solution | Coupon[a] | % Inhibition | Average % Inhibition |
|---|---|---|---|
| QI80-E | A | 80.4 | 81.0 |
|  | B | 81.6 |  |
| ARMOHIB219 | A | 81.9 | 82.7 |
|  | B | 83.5 |  |

According to the results in Table 4, the synthesized inhibitors (compounds 5, 8 and 10) appear to impart similar or even better (e.g. compound 8) protection than the two commercial imidazolines QI80-E and ARMOHIB219.

Example 12

Electrochemical Measurements: Tafel Extrapolation Method

The polarization studies were carried out in a 250 cm³ of 0.5 M NaCl solution in the presence of $CO_2$ (1 atm) in the absence and presence of 200 ppm inhibitors at 40° C. The experiments were started only after a stable open circuit potential (OCP) was achieved usually within the exposure time of 30 min. The electrochemical cell, assembled in a 750 cm³ round-bottomed flask, consisted of a saturated calomel electrode (SCE) as a reference electrode, mild steel working electrode, and the graphite counter electrode (~5 mm diameter). The Bubbler has one outlet and inlet for the $CO_2$. The SCE electrode was connected to the cell using a Luggin-Haber capillary salt bridge, the tip of which was separated from the surface of the working electrode by a distance of ≈2 mm. An electrometer was used to connect all three electrodes to a Potentiostat (Model 283, EG&G PARC). A rate of 1.6 mV/s was used to scan a range of ±250 mV with respect to open circuit potential.

The results of the Tafel plot extrapolation for mild steel in 1 M HCl (blank) at 60° C. or 0.5 M NaCl (blank) solutions containing various concentrations of the inhibitors at 40° C. in the presence of $CO_2$ (1 atm) are summarized in Tables 5 and 6. Some representative Tafel plots for the inhibition in 1 M HCl and in $CO_2$-saturated 0.5 M NaCl are shown in FIGS. 4 and 5a-5d, respectively.

TABLE 5

Results of Tafel plots in solutions containing 10 ppm of inhibitor in 1M HCl at 60° C.

| | Tafel plots | | | | | Polarization resistance | |
|---|---|---|---|---|---|---|---|
| Sample | $E_{corr}$ vs SCE (mV) | $\beta_a$ (mV/dec) | $\beta_C$ (mV/dec) | $i_{corr}$ (μA/cm²) | % IE | $R_p$ (Ω cm²) | η %[a] |
| Blank[a] | -457 | 9534 | 125 | 739 | — | 33.0 | — |
| 5 | -414 | 67.1 | 98.5 | 114 | 84.6 | 180 | 81.7 |
| 8 | -409 | 55.0 | 81.9 | 57.6 | 92.2 | 248 | 86.7 |
| 10 | -407 | 59.6 | 103 | 65.6 | 91.2 | 250 | 86.8 |

[a]The blank was a 1M HCl solution.
[b]Inhibition Efficiency, IE (i.e. η) = surface coverage θ.

TABLE 6

Results of Tafel plots of a mild steel sample in various solutions containing inhibitor in 0.5M NaCl saturated with $CO_2$ at 40° C.

| | | Tafel plots | | | |
|---|---|---|---|---|---|
| Sample | Concentration (ppm) | $E_{corr}$ vs. SCE (mV) | $\beta_a$ (mV/dec) | $\beta_C$ (mV/dec) | $i_{corr}$ (μA/cm²) | η %[a] |
| Blank[b] | 0 | -695 | 67.1 | 580 | 147 | — |
| 5 | 1.5 | -659 | 66.1 | 510 | 67.5 | 54.1 |
|  | 2.5 | -650 | 65.5 | 418 | 54.9 | 62.7 |
|  | 5 | -647 | 52.0 | 385 | 49.2 | 66.6 |
|  | 10 | -645 | 43.5 | 300 | 38.4 | 73.9 |
|  | 25 | -640 | 34.7 | 227 | 22.4 | 84.8 |
|  | 100 | -606 | 36.8 | 247 | 7.90 | 94.6 |
|  | 200 | -601 | 35.6 | 233 | 6.50 | 95.5 |
| 8 | 0.5 | -681 | 94.5 | 643 | 82.4 | 44.0 |
|  | 1 | -649 | 77.8 | 337 | 47.9 | 67.4 |
|  | 1.5 | -646 | 67.4 | 277 | 33.5 | 77.2 |
|  | 2.5 | -641 | 60.6 | 228 | 17.5 | 88.1 |
|  | 5 | -633 | 93.8 | 265 | 16.3 | 88.9 |
|  | 10 | -630 | 88.8 | 255 | 14.1 | 90.4 |
|  | 25 | -621 | 81.4 | 238 | 10.2 | 93.1 |
|  | 100[c] | -617 | 73.1 | 213 | 8.25 | 94.4 |
|  | 200[c] | -607 | 77.3 | 207 | 6.50 | 95.6 |
| 10 | 0.5 | -690 | 68.7 | 670 | 100 | 32.0 |
|  | 1 | -686 | 61.4 | 376 | 70.5 | 52.0 |
|  | 1.5 | -681 | 69.8 | 344 | 45.6 | 69.0 |
|  | 2.5 | -646 | 117 | 259 | 17.9 | 87.9 |
|  | 5 | -635 | 123 | 360 | 14.9 | 89.9 |
|  | 10 | -634 | 97.9 | 279 | 12.1 | 91.8 |
|  | 15 | -618 | 110 | 243 | 10.4 | 92.9 |
|  | 25 | -610 | 93.9 | 241 | 8.00 | 94.6 |
|  | 50 | -596 | 128 | 289 | 6.65 | 95.5 |
|  | 100 | -590 | 130 | 280 | 2.88 | 98.0 |
|  | 200 | -586 | 125 | 275 | 2.25 | 98.5 |

[a]Inhibition Efficiency, IE (i.e. η) = surface coverage θ.
[b]The blank was a 0.5M NaCl solution saturated with $CO_2$.
[c]Cloudy solution.

The results for the η % of the synthesized compounds (10 ppm) in 1 M HCl by Tafel extrapolations in Table 5 corroborated the results from the weight loss method shown in Table 1. Significant lowering of the $i_{corr}$ values confirms the inhibitive nature of the synthesized molecules. In the presence of the inhibitor molecules, the shifting of the $E_{corr}$ in the positive direction 1 M HCl suggests that the synthesized molecules are anodic type inhibitors which mainly suppress the anodic reaction.

In the case of a shift of OCP by at least 85 mV in the presence of an inhibitor, it can be classified as a cathodic or anodic type inhibitor (O. L. Riggs, Jr. Corrosion Inhibitors, 2nd edn, C. C. Nathan, Houston, Tex., 1973—incorporated herein by reference in its entirety). Due to the moderate displacement of 43 to 50 mV (Table 5) in the positive direction, compounds 5, 8 and 10 may not be considered as anodic type inhibitors. The more pronounced decrease in the anodic current densities is indicative of the greater decrease in the anodic oxidation rate than the rate of hydrogen evolution in the cathodic reaction. The inhibitors did not influence the corrosion reactions as indicated by the decreased values of slopes $\beta_C$ and $\beta_a$. Instead, they formed a barrier film on the metal surface. The above results suggest that the inhibitors are acting as mixed-type inhibitors under the predominance of anodic control. The high η % may be attributed to the beneficial role of the π- and non-bonded electrons, hydrophobic alkyl chain, and the cinnamaldehyde group. These polarizable electrons assist the adsorption of the inhibitor molecules on the anodic sites through their interaction with the d-orbitals of iron or $Fe^{2+}$.

Example 13

Electrochemical Measurements: Linear Polarization Resistance (LPR) Method

The cell described above was also used for the LPR measurement. The current potential plots (in a range of ±10 mV around $E_{corr}$) provided the polarization resistance values described below.

The η % from LPR technique was calculated using Equation 5:

$$\eta\ (\%) = \left(\frac{R'_p - R_p}{R'_p}\right) \times 100 \quad \text{(Equation 5)}$$

where $R_p$ and $R'_p$ are the respective polarization resistances in the absence and presence of the inhibitors in 1 M HCl at 60° C. and $CO_2$-saturated 0.5 M NaCl at 40° C. (Tables 5 and 7).

TABLE 7

Results of the LPR method in 0.5M NaCl saturated with $CO_2$ at 40° C.

| Sample | Concentration (ppm) | $R'_p$ ($\Omega\ cm^2$) | $\theta^a$ | θ % |
|---|---|---|---|---|
| Blank[b] | 0 | 129 | — | — |
| 5 | 1.5 | 343 | 0.623 | 62.3 |
|   | 2.5 | 613 | 0.79 | 79.0 |
|   | 5 | 689 | 0.813 | 81.3 |
|   | 10 | 790 | 0.837 | 83.7 |
|   | 25 | 980 | 0.868 | 86.8 |
|   | 100 | 1057 | 0.878 | 87.8 |
|   | 200 | 1360 | 0.905 | 90.5 |
| 8 | 1 | 351 | 0.632 | 63.2 |
|   | 1.5 | 466 | 0.723 | 72.3 |
|   | 2.5 | 763 | 0.831 | 83.1 |
|   | 5 | 832 | 0.845 | 84.5 |
|   | 10 | 1142 | 0.887 | 88.7 |
|   | 25 | 1573 | 0.918 | 91.8 |
|   | 100 | 3071 | 0.958 | 95.8 |
|   | 200 | 5864 | 0.978 | 97.8 |
| 10 | 0.5 | 318 | 0.594 | 59.4 |
|   | 1 | 357 | 0.639 | 63.9 |
|   | 1.5 | 379 | 0.783 | 78.3 |
|   | 2.5 | 1313 | 0.902 | 90.2 |
|   | 5 | 1575 | 0.918 | 91.8 |
|   | 10 | 1631 | 0.921 | 92.1 |
|   | 15 | 2186 | 0.941 | 94.1 |
|   | 25 | 3520 | 0.963 | 96.3 |
|   | 50 | 5314 | 0.976 | 97.6 |
|   | 100 | 5358 | 0.976 | 97.6 |
|   | 200 | 5480 | 0.976 | 97.6 |

[a] Surface coverage, θ = Inhibition Efficiency, IE (i.e. η).
[b] 0.5M NaCl saturated with $CO_2$.

The LPR (Table 7) and Tafel (Tables 5 and 6) data corroborated the results obtained from the gravimetric method (Table 3).

The results from the Tafel extrapolation and LPR in $CO_2$-saturated 0.5 M NaCl in the presence of various concentrations of the inhibitors are given in Tables 6 and 7, respectively. The presence of inhibitors lowers the corrosion current density largely for the anodic branch than for the cathodic lines, thereby indicating the greater suppression of the anodic dissolution of the iron than the cathodic evolution of $H_2$ (FIGS. 5a-5d). It appears that the inhibitor has shifted the $E_{corr}$ in the positive direction in $CO_2$ saturated 0.5 M NaCl (FIGS. 5a-5d, Table 6). The $E_{corr}$ values have shifted more than 85 mV in the positive direction in the higher concentration range for all three inhibitors. As a result, the compounds can be classified as anodic type inhibitors (P. C. Okafor, X. Liu, Y. G. Zheng, Corrosion inhibition of mild steel by ethylamino imidazoline derivative in $CO_2$-saturated solution, Corros. Sci. 51 (2009) 761-768—incorporated herein by reference in its entirety). This is supported by the observed increase in the anodic slopes ($\beta_a$) in the presence of the inhibitors, thereby confirming the influence of the inhibitors to suppress the anodic reactions.

A negative or a positive value for the molecular interaction constant f indicates repulsion or attraction, respectively, among the adsorbed molecules (A. Yurt, G. Bereket, A. Kivrak, A. Balaban, B. Erk, Effect of Schiff Bases Containing Pyridyl Group as Corrosion Inhibitors for Low Carbon Steel in 0.1 M HCl, J. Appl. Electrochem. 35 (2005) 1025-1032—incorporated herein by reference in its entirety). The relatively lower values off observed in 1 M HCl, 0.5 M $H_2SO_4$ as well as in $CO_2$-saturated 0.5 M NaCl indicate that there may be some van der Waal attractive forces among the hydrophobic nonamethylene chain (Table 6).

Example 14

Adsorption Isotherms

Surface coverage (θ, i.e. fractional inhibition efficiency 17) values for compounds 5, 8 and 10 are reported in Tables 1-7. The η is directly related to the surface coverage θ of the electrode by an inhibitor molecule at its lower concentration, i.e. η %=θ %. However, a transition from a monolayer to a multilayer coverage at higher inhibitor concentrations no longer kept the relationship linear. The θ values obtained by gravimetric method in 1 M HCl (Table 1), and in 0.5 M $H_2SO_4$ (Table 2) and by Tafel extrapolations in $CO_2$-saturated 0.5 M NaCl (Table 6) and C (the concentration in mol/L) were used to find the best among the more frequently used adsorption isotherm, namely:

$$\text{Temkin: } K_{ads}C = e^{f\theta} \quad \text{(Equation 6)}$$

$$\text{Langmuir: } \theta/(1-\theta) = K_{ads}C \quad \text{(Equation 7)}$$

$$\text{Frumkin: } K_{ads}C = \{\theta/(1-\theta)\}e^{-2a\theta} \quad \text{(Equation 8)}$$

(A. N. Frumkin, Die Kapillarkurve der höheren Fettsäuren und die Zustandsgleichung der Oberflächenschicht, Z. Phys. Chem. 116 (1925) 466-484—incorporated herein by reference in its entirety).

$$\text{Freundlich: } \theta = K_{ads}C^n \quad \text{(Equation 9)}$$

Figure 6A:
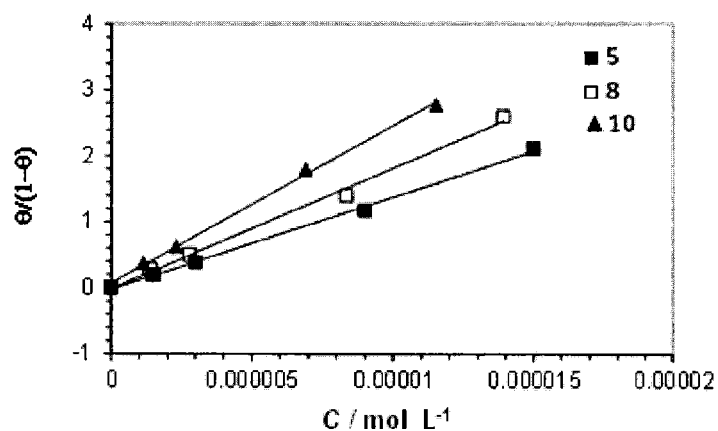
FIG. 6a shows Langmuir adsorption isotherm plots of compounds 5, 8 or 10 in 1 M HCl at 60° C.
Figure 6B:
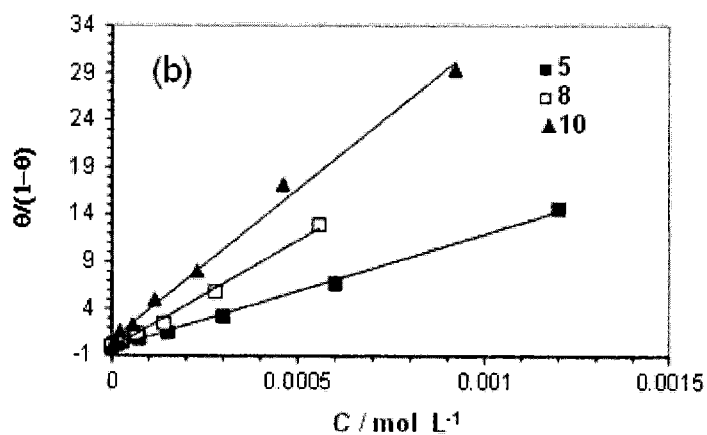
FIG. 6b shows Langmuir adsorption isotherm plots of compounds 5, 8 or 10 in 0.5 M $H_2SO_4$ at 60° C.
Figure 6C:
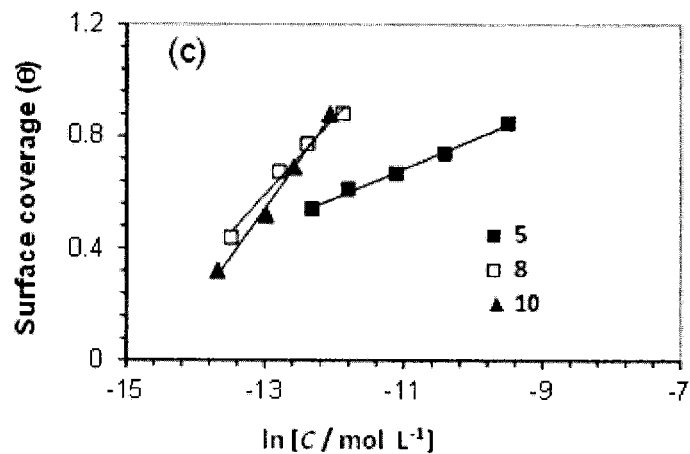
FIG. 6c shows Temkin adsorption isotherm plots of compounds 5, 8 or 10 in $CO_2$ saturated 0.5 M NaCl at 40° C.

(J. O'M. Bockris, S. U. M. Khan, Surface Electrochemistry: A Molecular Level approach, Plenum press, New York and London, 1993—incorporated herein by reference in its entirety). where $K_{ads}$ is the equilibrium constant of the adsorption process. As shown in Table 8 below and also FIGS. 6a-6c, the correlation coefficient indicated the best fit for the Langmuir isotherm for the inhibitors in 1 M HCl (FIG. 6a) as well as in 0.5 M $H_2SO_4$ (FIG. 6b) and Temkin isotherm in $CO_2$ saturated 0.5 M NaCl (FIG. 6c). Some of the inhibitor molecules gave good fit for both the Temkin as well as Langmuir adsorption isotherms. The molecular interaction parameter f was calculated from linear fitting slope of 1/f in Table 8 (A. N. Frumkin, Die Kapillarkurve der höheren Fettsäuren und die Zustandsgleichung der Oberflächenschicht, Z. Phys. Chem. 116 (1925) 466-484—incorporated herein by reference in its entirety).

TABLE 8

The square of correlation coefficients ($R^2$) and values of the constants (a and f) in various adsorption isotherms in the presence of inhibitors.

| Compound | Temkin ($R^2$, f) | Frumkin ($R^2$, a) | Langmuir ($R^2$) | Freundlich ($R^2$) |
|---|---|---|---|---|
| in 1M HCl (60° C.) (Gravimetry) | | | | |
| 5 | 0.9923, 4.45 | 0.4096 | 0.9975 | 0.9936 |
| 8 | 0.9942, 4.52 | 0.1844 | 0.9958 | 0.9950 |
| 10 | 0.9953, 4.84 | 0.8319, −0.27 | 0.9972 | 0.9923 |
| in 0.5M $H_2SO_4$ (60° C.) (Gravimetry) | | | | |
| 5 | 0.9916, 5.65 | 0.4158 | 0.9972 | 0.9521 |
| 8 | 0.9935, 5.52 | 0.4148 | 0.9944 | 0.9097 |
| 10 | 0.9167, 7.87 | 0.5793 | 0.9934 | 0.8351 |
| in 0.5M NaCl/$CO_2$ (40° C.) (Tafel) | | | | |
| 5 (Tafel) | 0.9942, 9.47 | 0.9499, −2.18 | 0.9568 | 0.9907 |
| 8 (Tafel) | 0.9859, 3.64 | 0.9580, +0.680 | 0.9706 | 0.9544 |
| 10 (Tafel) | 0.9936, 2.86 | 0.9010, +1.00 | 0.8861 | 0.9916 |
| 10 (LPR) | 0.9955, 3.45 | 0.8741, +0.89 | 0.9324 | 0.9811 |

The $K_{ads}$ is related to the free energy of adsorption ($\Delta G°_{ads}$), by:

$$K_{ads} = \frac{1}{55.5} \exp\left(\frac{-\Delta G°_{ads}}{RT}\right) \quad \text{(Equation 10)}$$

The values of $K_{ads}$ and $\Delta G°_{ads}$ are summarized in Table 9.

TABLE 9

Thermodynamic parameters of the mild steel dissolution in the presence of compounds 5, 8 or 10.

| Compound | Isotherm used | $K_{ads}$ L/mol | $\Delta G°_{ads}$ kJ/mol |
|---|---|---|---|
| in 1M HCl (60° C.) (Gravimetry) | | | |
| 5 | Langmuir | 1.40E+5 | −43.9 |
| 8 | Langmuir | 1.83E+5 | −44.6 |
| 10 | Langmuir | 2.39E+5 | −45.4 |
| in 0.5M $H_2SO_4$ (60° C.) (Gravimetry) | | | |
| 5 | Langmuir | 1.21E+4 | −37.1 |
| 8 | Langmuir | 2.29E+4 | −38.9 |
| 10 | Langmuir | 3.20E+4 | −39.8 |
| in 0.5M NaCl/$CO_2$ (40° C.) (Tafel) | | | |
| 5 (Tafel) | Temkin | 3.89E+7 | −59.5 |
| 8 (Tafel) | Temkin | 4.07E+6 | −53.1 |
| 10 (Tafel) | Temkin | 2.07E+6 | −51.4 |
| 10 (LPR) | Temkin | 4.02E+6 | −53.2 |

The negative values of $\Delta G°_{ads}$ in Table 8 ensure the spontaneity of the adsorption process. Generally, values of $\Delta G°_{ads}$ up to −20 kJ/mol and in the range −80 to −400 kJ/mol are attributed to physisorption and chemisorption, respectively. The calculated $\Delta G°_{ads}$ values in the range 51-60 kJ/mol in 1M HCl, 37-40 kJ/mol in 0.5 M $H_2SO_4$ and 44-45 kJ/mol in $CO_2$-saturated 0.5 M NaCl indicate, therefore, that the inhibitor molecules in various media undergo a combination of both electrostatic adsorption and chemisorption (S. Z. Duan, Y. L. Tao, Interface Chemistry, Higher Education Press, Beijing, 1990; V. Branzoi, M. Baibarac, F. Branzoi, The inhibition action of sodium salts of some organic acids on the corrosion of armco iron in $H_2SO_4$ and HCl solutions, Scientific Bulletin University Politehnica of Bucharest, Sci Bull B Chem Mater. Sci. 63 (2001) 9-17—each incorporated herein by reference in its entirety). The presence of a variety of π- and non-bonded electrons helps the inhibitor molecules to interact with the anodic sites via overlapping with the low lying vacant d-orbitals of iron.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. A composition for inhibiting corrosion of mild steel, comprising
   at least one acid selected from the group consisting of HCl, $H_2SO_4$, and $HNO_3$, and
   a compound having the following Formulas I or II:

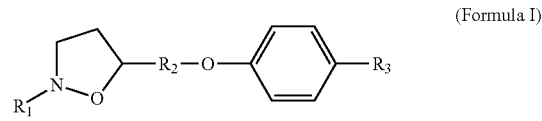

(Formula I)

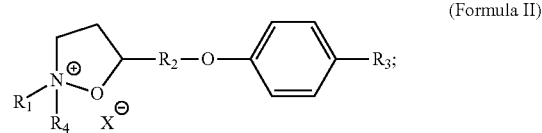

(Formula II)

wherein:
$R_1$ is selected from the group consisting of hydrogen, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkyl, and substituted or unsubstituted heterocycloalkyl;
$R_2$ is selected from the group consisting of substituted or unsubstituted, branched or linear, $C_{1-22}$ alkyl, substituted or unsubstituted $C_{1-22}$ haloalkyl, substituted or unsubstituted $C_{2-22}$ alkenyl and substituted or unsubstituted $C_{2-22}$ alkynyl;
$R_3$ is selected from the group consisting of substituted or unsubstituted $C_{1-12}$ aldehyde, substituted or unsubstituted acrylic acid, substituted or unsubstituted propanol and substituted or unsubstituted propenal;
$R_4$ is selected from the group consisting of substituted or unsubstituted, branched or linear, $C_{2-22}$ alkynyl; and
X is selected from the group consisting of fluoride, chloride, bromide and iodide.

2. The composition of claim 1, wherein the compound is selected from the group consisting of:

p-9-(2-methylisoxazolidin-5-yl)undec-1-yloxybenzaldehyde;

p-9-(2-methylisoxazolidin-5-yl)non-1-yloxycinnamaldehyde; and p-9-[2-methyl-2-(2-popyn-1-yl) isoxazolidinium-5-yl] non-1-yloxycinnamaldehyde chloride.

3. The composition of claim 1, further comprising at least one selected from the group consisting of $CO_2$ and HS.

4. The composition of claim 1, wherein the compound is present in the composition at a concentration of 10 to 1000 parts by the total weight of the composition.

5. A method of inhibiting the corrosion of mild steel, comprising:

contacting the mild steel with a composition comprising at least one acid selected from the group consisting of HCl, $H_2SO_4$ and $HNO_3$, and a compound having the following Formulas I or II:

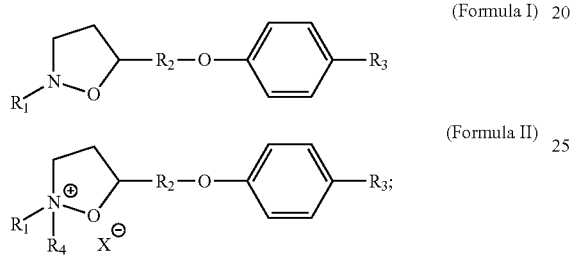

wherein:

$R_1$ is selected from the group consisting of hydrogen, substituted or unsubstituted $C_{1-12}$ alkyl, substituted or unsubstituted $C_{1-12}$ haloalkyl, substituted or unsubstituted $C_{2-12}$ alkenyl, substituted or unsubstituted $C_{2-12}$ alkynyl, substituted or unsubstituted aryl, substituted or unsubstituted cycloalkyl, substituted or unsubstituted heteroaryl, substituted or unsubstituted heterocycloalkyl, substituted or unsubstituted arylalkyl, substituted or unsubstituted heteroarylalkyl, substituted or unsubstituted cycloalkyl, and substituted or unsubstituted heterocycloalkyl;

$R_2$ is selected from the group consisting of substituted or unsubstituted, branched or linear $C_{1-22}$ alkyl, substituted or unsubstituted $C_{1-22}$ haloalkyl, substituted or unsubstituted $C_{2-22}$ alkenyl and substituted or unsubstituted $C_{2-22}$ alkynyl;

$R_3$ is selected from the group consisting of substituted or unsubstituted $C_{1-12}$ aldehyde, substituted or unsubstituted acrylic acid, substituted or unsubstituted propanol and substituted or unsubstituted propenal;

$R_4$ is selected from the group consisting of substituted or unsubstituted, branched or linear, $C_{2-22}$ alkynyl; and X is selected from the group consisting of fluoride, chloride, bromide and iodide.

6. The method of claim 1, wherein the compound is selected from the group consisting of:

p-9-(2-methylisoxazolidin-5-yl)undec-1-yloxybenzaldehyde;

p-9-(2-methylisoxazolidin-5-yl)non-1-yloxycinnamaldehyde; and p-9-[2-methyl-2-(2-popyn-1-yl) isoxazolidinium-5-yl] non-1-yloxycinnamaldehyde chloride.

7. The method of claim 5, wherein the mild steel is contacted with the composition at a temperature greater than 140° C.

8. The method of claim 5, wherein the mild steel is contacted with the composition at a pressure of 700-1,000 bar.

* * * * *